United States Patent
Zee et al.

(10) Patent No.: US 7,960,352 B2
(45) Date of Patent: Jun. 14, 2011

(54) **ANTI-CANCER ACTIVITY OF *ANDROSACE UMBELLATA MERR.* EXTRACT AND CONTAINED TRITERPENE SAPONIN**

(75) Inventors: Ok Pyo Zee, Seoul (KR); Se Chan Kang, Gunpo-si (KR); Jon g Hwan Kwak, Suwon-si (KR); Joa Sub Oh, Seoul (KR); Han Choi, Suwon-si (KR); Jong Phil Bak, Hwaseong-si (KR); Chang Min Lee, Suwon-si (KR); Yong Joon Cheong, Gyeonggi-do (KR)

(73) Assignee: Sungkyunkwan University Foundation for Corporate Collaboration, Gyeonggi-Do (KR)

( * ) Notice: Subject to any disclaimer, the term of this patent is extended or adjusted under 35 U.S.C. 154(b) by 299 days.

(21) Appl. No.: 12/067,869

(22) PCT Filed: Sep. 14, 2006

(86) PCT No.: PCT/KR2006/003668
§ 371 (c)(1),
(2), (4) Date: Jun. 17, 2008

(87) PCT Pub. No.: WO2007/037598
PCT Pub. Date: Apr. 5, 2007

(65) Prior Publication Data
US 2008/0280839 A1    Nov. 13, 2008

(30) Foreign Application Priority Data
Sep. 29, 2005 (KR) .................. 10-2005-0091442

(51) Int. Cl.
*A61K 31/702* (2006.01)
*A61K 31/045* (2006.01)
*A61P 35/00* (2006.01)

(52) U.S. Cl. ......................................................... 514/27
(58) Field of Classification Search .................. None
See application file for complete search history.

(56) References Cited

OTHER PUBLICATIONS

Zhang, D.-M., Biochemical and Biophysical Research Communications, vol. 362, pp. 759-765 (2007).*
MayoClinic.com "cancer"; also available at http://www.mayoclinic.com/health/cancer/DS01076; last viewed Aug. 4, 2010.*
Developmental Therapeutics Program: NCI/NIH "Screening Services: Cell Lines In The In Vitro Screen"; also available at http://web.archive.org/web/20041017072850/http://www.dtp.nci.nih.gov/docs/misc/common_files/cell_list.html; published electronically Oct. 17, 2004.*
National Cancer Institute, SEER Program "Five Most Common Cancers in Each Racial/Ethnic Group"; available at http://web.archive.org/web/20030309225131/http://seer.cancer.gov/publications/ethnicity/topfive.pdf; published electronically Mar. 9, 2003.*
Stephen J. Bloor, Cytotoxic Saponins From New Zealand Myrsine Species, J. Nat. Prod., 57 (10), pp. 1354-1360 (1994).
Jonathan P. Waltho, et al., Structure Elucidation of Two Triterpenoid Tetrasaccharides From *Androsace saxifragifolia*, J. Chem. Soc. Perkin. Trans. I, 98), pp. 1527-1531 (1986).
Bikas C. Pal, et al., New Triterpenoid Pentasaccharides From *Androsace saxifragifolia*, J. Chem. Soc. Perkin. Trans. I, (9), pp. 1963-1967 (1987).

* cited by examiner

*Primary Examiner* — Shaojia Anna Jiang
*Assistant Examiner* — Bahar Schmidtmann
(74) *Attorney, Agent, or Firm* — Frommer Lawrence & Haug LLP; Ronald R. Santucci

(57) ABSTRACT

The present invention relates to an *Androsace umbellata* Merr. extract having anticancer activity and a triterpene saponin compound isolated therefrom, more particularly to an *Androsace umbellata* (Lour.) Merr. extract, triterpene saponin compounds isolated therefrom, saxifragifolin B and saxifragifolin D, which inhibit the growth of cancer cells and induce apoptosis of cancer cells, and thus are useful for preparing a composition for preventing and treating cancers and a method of isolating a triterpene saponin compound from an *Androsace umbellata* Merr. extract.

5 Claims, 3 Drawing Sheets

Fig. 3

```
                    Butanol fraction (22g)
                              |
                    SiO₂ vacuum flash column
                    (methylene chloride : MeOH : D.W. = 40:10:1, 70:30:3)
    ┌──────────┬──────────┬──────────┬──────────┬──────────┬──────────┐
Fraction 1  Fraction 2  Fraction 3  Fraction 4  Fraction 5  Fraction 6  Fraction 7
 (524mg)    (1.065g)    (494mg)     (513mg)     (2.776g)    (7.770g)    (1.758g)
                                                    |           |
                                            1) Sephadex LH-20   1) Sephadex LH-20
                                               (70% MeOH)          (70% MeOH)
                                            2) RP-18            2) RP-18
                                               (65% MeOH)          (65% MeOH)
                                            3) Recycling HPLC   3) Recycling HPLC
                                               (100% MeOH)         (70% MeOH)

Saxifragifolin B    Saxifragifolin D
```

ANTI-CANCER ACTIVITY OF *ANDROSACE UMBELLATA MERR.* EXTRACT AND CONTAINED TRITERPENE SAPONIN

This application is a 371 of PCT/KR2006/003668 filed on Sep. 14, 2006, published on Apr. 5, 2007 under publication number WO 2007/037598 A1 which claims priority benefits from South Korean Patent Application Number 10-2005-0091442 filed Sep. 29, 2005, the disclosure of which is hereby incorporated by reference.

TECHNICAL FIELD

The present invention relates to an *Androsace umbellata* Merr. extract having anticancer activity and a triterpene saponin compound isolated therefrom. In particular, the present invention relates to an *Androsace umbellata* (Lour.) Merr. extract, triterpene saponin compounds isolated therefrom, saxifragifolin B and saxifragifolin D, which inhibit the growth of cancer cells and induce apoptosis of cancer cells, and thus are useful for a composition for preventing and treating cancers and a method of isolating a triterpene saponin compound from an *Androsace umbellata* Merr. extract.

BACKGROUND ART

Cancer refers to a collective class of diseases characterized by uncontrolled proliferation of cells and their invasion to normal tissues or organs caused by the accumulation of genetic mutations, thereby destroying the normal tissues or organs, generating new sites of malignancy and, in the end, leading to death of an organism.

At present, chemotherapy using anticancer compounds largely depends on about 40 kinds of anticancer compounds having strong cytotoxicities and thus causes many side effects. Therefore, there is a need for the development of new anticancer agents that can effectively treat cancers with no or much reduced side effects. In this regard, researches have been focused on developing new anticancer agents using natural products, particularly from wild plants and herbs. Of the anticancer agents originated from natural products, there is Taxol (paclitaxel) isolated from the Pacific yew tree. However, this compound is not advantageous in that it affects not only the cancer cells but also normal cells and also has toxicity and side effects because of its low solubility in water.

The present inventors, in the midst of conducting researches to find anticancer agents, discovered that an *Androsace umbellata* Merr. extract, a solvent fraction thereof and saxifragifolin isolated therefrom can inhibit various cancer cells, which have never been reported. There is a report that the root extract of *Ardisia crispa* induces uterine contraction in mice and saxifragifolin D and saxifragifolin B were isolated as an active ingredient. However, there has been no report on their role in preventing or treating cancers and tumors [Baumann et al., Ardisiacrispin A and B, two utero-contracting saponins from *Ardisia crispa*. *Planta Medica*, 53, 405-409, 1987.].

The present inventors have made extreme efforts to find herbal compounds providing better anticancer activities than those of the existing known anticancer agents while having less side effects. As a result, they confirmed that the *Androsace umbellata* Merr. extract, the fraction thereof and the triterpene saponin compounds isolated therefrom have superior anticancer activities against lung cancer, breast cancer, uterine cancer, colon cancer, etc.

DISCLOSURE OF THE INVENTION

Accordingly, an object of the present invention is to provide an *Androsace umbellata* Merr. extract, a fraction thereof and an anticancer agent comprising a triterpene saponin compound isolated therefrom as an active ingredient.

Another object of the present invention is to provide a method of isolating a triterpene saponin compound, which is effective in treating and preventing cancers, from *Androsace umbellata* Merr.

The present invention relates to an *Androsace umbellata* Merr. extract, a fraction and an anticancer agent comprising saxifragifolin B, saxifragifolin D or a mixture thereof as an active ingredient.

The present invention also relates to a method of isolating a triterpene saponin compound, which is effective in treating and preventing cancers, from *Androsace umbellata* Merr.

Hereinafter, the present invention is described in more detail.

The present invention relates to an *Androsace umbellata* (Lour.) Merr. extract, triterpene saponin compounds isolated therefrom, saxifragifolin B and saxifragifolin D, which are confirmed to inhibit the growth of cancer cells and induce the apoptosis of cancer cells, and a method of isolating a triterpene saponin compound from the *Androsace umbellata* Merr. extract.

Saxifragifolin D (cyclamiretin A 3-O-{β-D-glucopyranosyl-(1→4)-β-D-glucopyranosyl-(1→2)-β-D-xylopyranosyl-(1→2)-β-D-glucopyranosyl-(1→4)-α-L-arabinopyranoside}) and saxifragifolin B (cyclamiretin A 3-O-{β-D-xylopyranosyl-(1→2)-β-D-glucopyranosyl-(1→4)-β-D-glucopyranosyl-(1→2)-α-L-arabinopyranoside}) which are derived from *Androsace umbellata* Merr. of the Primulaceae family are the compounds represented by the formulas (1) and (2) below. They can be obtained from *Androsace umbellata* Merr. by the method described below.

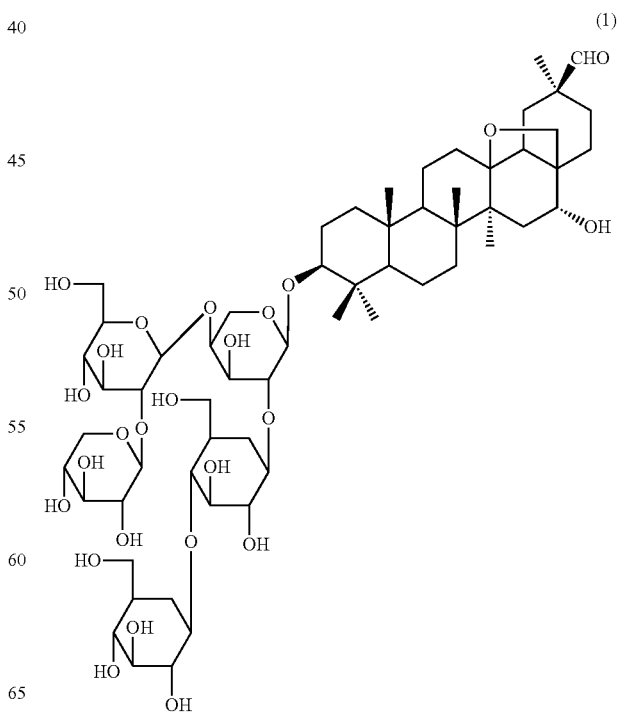

(1)

-continued (2)

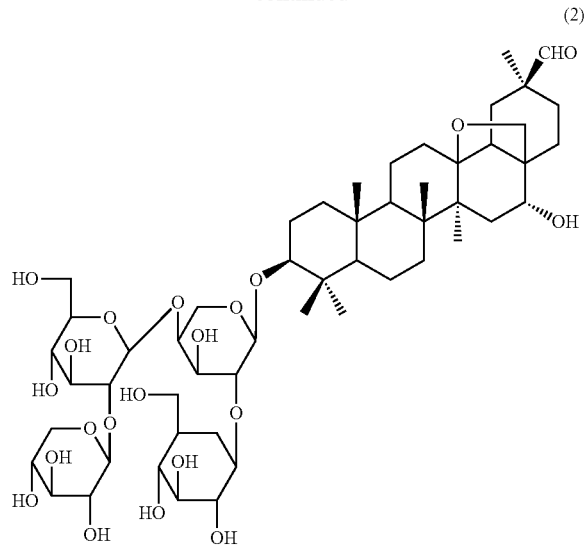

The present invention provides a method of isolating the triterpene saponin compound from *Androsace umbellata* Merr., comprising:

1) mincing *Androsace umbellata* Merr., extracting with a $C_1$-$C_4$ low grade alcohol, water or a mixed solvent thereof, filtering and concentrating the filtrate under reduced pressure to obtain an extract;

2) concentrating the alcohol extract, suspending it in water, fractionating with a solvent in the order of n-hexane dichloromethane, ethyl acetate and n-butanol and concentrating under reduced pressure to obtain a fraction;

3) loading the n-butanol fraction onto a silica gel column and eluting with a mixed solvent of dichloromethane, methanol and water;

4) eluting again with a mixed solvent of dichloromethane, methanol and water and finally washing with methanol to obtain an active fraction; and 5) performing Sephadex column chromatography and reverse phase column chromatography in sequence and purify the resultant by HPLC to obtain saxifragifolin B or saxifragifolin D from the active fraction.

Hereunder is given detailed description of each step.

First, *Androsace umbellata* Merr. is dried, and minced. Subsequently, *Androsace umbellata* Merr. is extracted with 1-100 equivalents (L), preferably 5-15 equivalents, of a $C_1$-$C_4$ low grade alcohol, water or a mixed solvent thereof, based on the weight (kg) of *Androsace umbellata* Merr., and filtered. The filtrate is concentrated under reduced pressure to obtain an *Androsace umbellata* Merr. extract. Preferred examples of the low grade alcohol include methanol, ethanol, propanol, isopropanol, n-butanol, etc.

The extract is concentrated to obtain 150-300 g of an extract, which is suspended in 0.5-3 L of distilled water. After fractionating in sequence with 0.3-3 equivalents, preferably 1 equivalent, of the suspension of n-hexane, dichloromethane, ethyl acetate and n-butanol, it is concentrated under reduced pressure to obtain 30-100 g of an n-butanol fraction.

The n-butanol fraction is eluted in a silica gel column using a mixed solvent of dichloromethane, methanol and water as an eluent. Preferably, a dichloromethane/methanol/water (100-50/50-10/5-1) mixed solvent is used as the eluent.

After washing with methanol, an active fraction containing saxifragifolins B and D is obtained with a yield of 30-70% of the n-butanol fraction.

Of the resultant active fraction, Sephadex LH-20 column chromatography (eluent: 30-100% methanol) and RP-18 reverse phase column chromatography (eluent: 55-70% methanol) are performed in sequence and then applied to recycling HPLC (JAIGEL GS-310 column) to obtain the saxifragifolin B-containing fraction equivalent to 20-50% of saxifragifolin B to be applied.

And, Sephadex LH-20 column chromatography (eluent: 30-100% methanol) and RP-18 reverse phase column chromatography (eluent: 55-70% methanol) are performed in sequence and then applied to recycling HPLC (JAIGEL GS-310 column) to obtain the saxifragifolin D-containing fraction equivalent to 20-50% of saxifragifolin D to be applied.

For the resultant *Androsace umbellata* Merr. alcohol extract, fraction thereof and saxifragifolin B and saxifragifolin D isolated therefrom, the capacity of inhibiting the growth and inducing the apoptosis of A549 (lung cancer cells), HCT15 (colon cancer cells), MCF7, MDA-MD-231 (breast cancer cells), HeLa, SK-OV-3 (uterine cancer cells), etc. was confirmed. Saxifragifolin B, saxifragifolin D and a mixture thereof had anticancer activity. That is, they were effective in inhibiting the growth and inducing the apoptosis of cancer cells.

Accordingly, the *Androsace umbellata* Merr. extract, fraction thereof and saxifragifolin B, saxifragifolin D or a mixture thereof can be effectively used to prevent and treat cancers.

Further, the *Androsace umbellata* Merr. extract, fraction thereof and saxifragifolin B and saxifragifolin D isolated therefrom can be prepared into oral administration forms, for example, tablets, troches, lozenges, water-soluble or oil-soluble suspensions, powder or granules, emulsions, hard or soft capsules, syrups or elixirs, as an active ingredient. Such preparation forms as tablets, capsules, etc. may comprise a binder such as lactose, saccharose, sorbitol, mannitol, starch, amylopectin, cellulose or gelatin; an excipient such as dicalcium phosphate; a disintegrant such as cornstarch or sweet-potato starch; and a lubricant such as magnesium stearate, calcium stearate, sodium stearylfumarate or polyethylene glycol wax. A capsule formulation may further comprise a liquid carrier such as fatty oil. The active ingredient may also be administered non-orally, for example, by subcutaneous injection, intravenous injection, intramuscular injection or intrathoracic injection. Non-oral administration forms are prepared by mixing the composition with a stabilizer or a buffer in water and filling the resulting solution in ampules or vials.

Effect dosage of the *Androsace umbellata* Merr. extract, fraction thereof or triterpene saponin compound isolated therefrom may be varied depending on the age, physical conditions, body weight, etc. of the patient. In general, a dosage in the range from 1 to 100 mg/kg (body weight)/day is preferable. The administration can be given once or several times a day, within the effective dosage range.

Further, the *Androsace umbellata* Merr. extract, fraction thereof or triterpene saponin compound isolated therefrom may be used in health food. Health food used as herein refers to the food prepared by adding the afore-mentioned active ingredient in beverages, teas, flavors, gums, cookies, etc. or making it in the form of capsule, powder, suspension, etc. Health food offers a special health-related effect when taken, but is without side effects, which may accompany the long-term use of medicines, since it is made from food.

DESCRIPTION OF DRAWINGS

FIG. 3 illustrates the process of obtaining saxifragifolin B and saxifragifolin D from an *Androsace umbellata* Merr. butanol fraction.

BEST MODE FOR CARRYING OUT THE INVENTION

Practical and preferred embodiments of the present invention are given in the following examples. However, it will be appreciated that those skilled in the art may, in consideration of this disclosure, make modifications and improvements within the spirit and scope of the present invention.

Preparative Example 1

Preparation of *Androsace umbellata* Merr. Extract

The whole plant of *Androsace umbellata* Merr. collected in Changnyeoung-gun, Gyeongsangnam-do was dried. The dried whole plant of *Androsace umbellata* Merr. was minced. 1.5 kg of the resultant *Androsace umbellata* Merr. was repeatedly extracted with 7-20 L of methanol for 2-5 times at room temperature to obtain an extract.

Preparative Example 2

Figure 2:
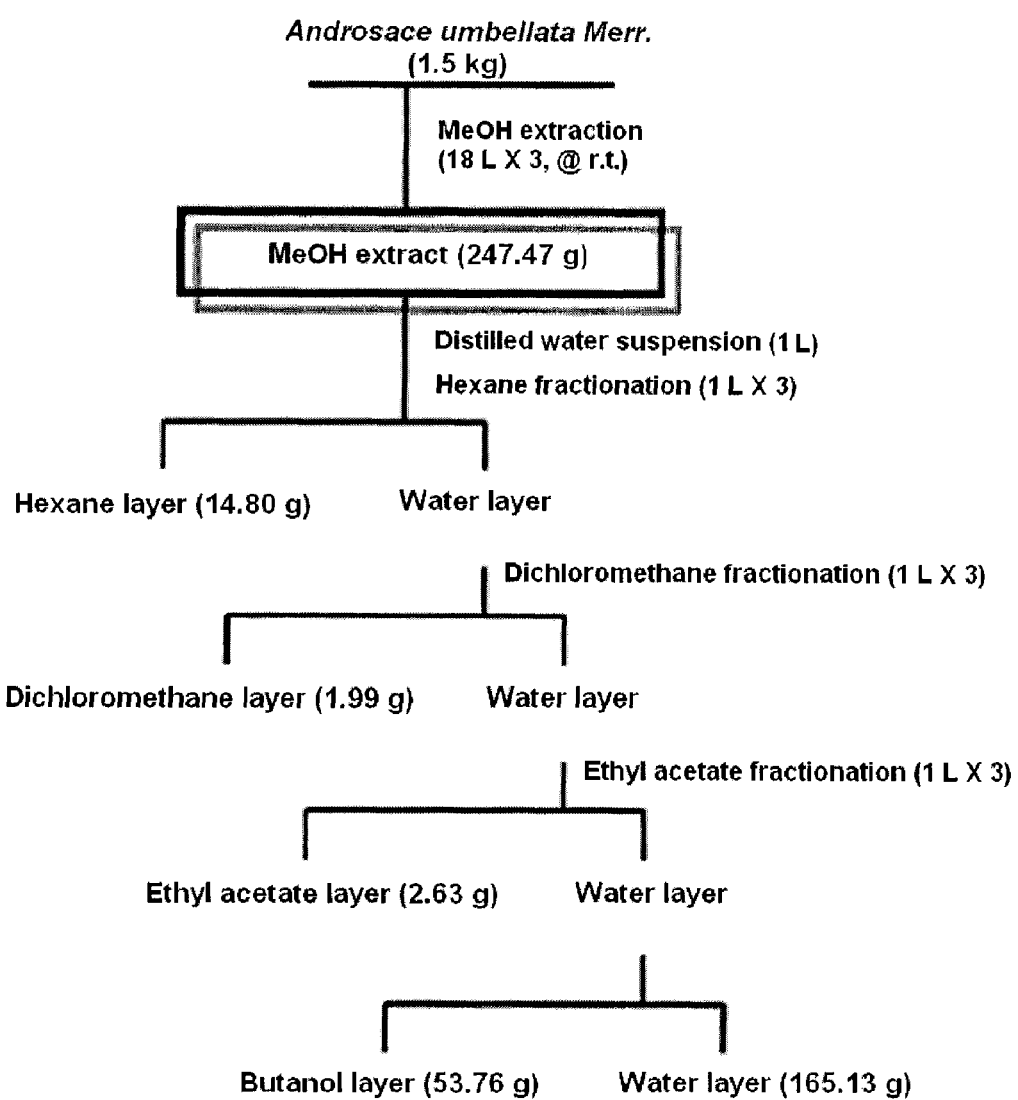
FIG. 2 illustrates the process of obtaining a butanol fraction from an *Androsace umbellata* Merr. extract.

Preparation of *Androsace umbellata* Merr. Fraction 247.47 g of the extract (methanol extract) obtained above was suspended in 2.5 L of distilled water, fractionated with the same volume of n-hexane, dichloromethane, ethyl acetate and n-butanol, in sequence, and concentrated under reduced pressure to obtain 53.76 g of a n-butanol fraction (see FIG. 2).

Preparative Example 3

Isolation of Saxifragifolin B and Saxifragifolin D 22 g of the n-butanol fraction obtained above was eluted using a silica gel column using a mixed solvent of dichloromethane, methanol and water (dichloromethane/methanol/water=100-50/50-10/5-1) as eluent. After washing with methanol, the active fractions containing saxifragifolins B and D were loaded onto a column to obtain 2.776 g and 7.770 g of fractions, respectively. Of the active fractions, Sephadex LH-20 column chromatography (eluent: 30-100% methanol), RP-18 reverse phase column chromatography (eluent: 55-70% methanol) and recycling HPLC (JAIGEL GS-310 column) were performed, in sequence, for 20 mg of the saxifragifolin B-containing fraction to obtain 6 mg of saxifragifolin B. And, Sephadex LH-20 column chromatography (eluent: 30-100% methanol), RP-18 reverse phase column chromatography (eluent: 53-70% methanol) and recycling HPLC (JAIGEL GS-310 column) were performed, in sequence, for 7.77 g of the saxifragifolin D-containing fraction to obtain 7 mg of saxifragifolin D (see FIG. 3).

Example 1

Inhibition of Growth of Tumor Cells

Cells were cultured in Dulbecco's modified Eagle's medium (hereunder referred to as DMEM) containing 5-10% fetal bovine serum and L-glutamine in an incubator of 37° C. and 5% $CO_2$. Adherent cells were suspended using a trypsin-EDTA solution and isolated and collected for testing.

The cells were cultured on a 96-well plate, $5 \times 10^3$-$10^4$ cells each. After treating with the extract and the active ingredient at a concentration of 0, 0.01, 0.1, 1, 10 and 100 μg/mL, the cells were cultured for 48 hours. After culturing for 24 hours, the culture medium was removed from each well and 200 μL of 10% TCA (trichloroacetic acid) was added. The cells were fixed to the bottom of the plate by letting alone at 4° C. for 1 hour. After fixation, the plate was washed with distilled water for 5-6 times to remove the remaining TCA solution and then completely dried. To the plate was added 200 μL of a staining solution per each well, which was prepared by dissolving 0.4% SRB solution in 1% acetic acid solution. After 30 minutes' staining, the plate was washed with 1% acetic acid solution for 5-6 times to remove excess SRB. The plate was dried at room temperature and 200 μL of 10 mM trisma base solution (unbuffered) was added per each well. After 10 minutes' of shaking using a titer plate shaker to elute out the staining solution, light absorbance was measured at 540 nm using a microplate reader.

Table 1 below shows the inhibitory effect against the growth of the A549, HCT15, MCF7, MDA-MB-231, HeLa and SK-OV-3 cells of the *Androsace umbellata* Merr. extract and fraction saxifragifolins B and D of the present invention.

TABLE 1

| Inhibitory effect against growth of cancer cells | | | | | | |
|---|---|---|---|---|---|---|
| | $IC_{50}$ (μg/mL) | | | | | |
| | A549 | HCT15 | MCF7 | SK-OV-3 | MDA-MB-231 | HeLa |
| MeOH extract | 0.810 ± 0.01 | 5.83 ± 0.38 | 89.82 ± 0.56 | 92.64 ± 0.29 | 22.49 ± 0.10 | 34.13 ± 0.12 |
| BuOH fraction | 0.085 ± 0.07 | 0.610 ± 0.54 | 19.58 ± 0.20 | 26.48 ± 0.39 | 5.80 ± 0.08 | 4.01 ± 0.08 |
| Saxifragifolin D | 0.016 ± 0.01 | 0.558 ± 0.24 | 3.23 ± 0.10 | 6.36 ± 0.12 | 1.32 ± 0.03 | 0.98 ± 0.05 |
| Saxifragifolin B | 0.036 ± 0.02 | 0.183 ± 0.17 | 6.88 ± 0.13 | 8.39 ± 0.23 | 3.02 ± 0.02 | 1.22 ± 0.04 |
| Doxorubicin (positive control) | 0.011 ± 0.01 | 0.014 ± 0.02 | 0.50 ± 0.02 | 0.77 ± 0.03 | 0.02 ± 0.01 | 0.21 ± 0.01 |

As seen in Table 1, the *Androsace umbellata* Merr. methanol extract, butanol fraction thereof and saxifragifolins B and D were effective in inhibiting the growth of cancer cells.

Example 2

Inducement of Apoptosis of Breast Cancer Cells

MCF7 cells were cultured in DMEM containing 5% fetal bovine serum and L-glutamine in an incubator of 37° C. and 5% $CO_2$. Adherent cells were suspended using a trypsin-EDTA solution and isolated and collected for testing.

Figure 1:
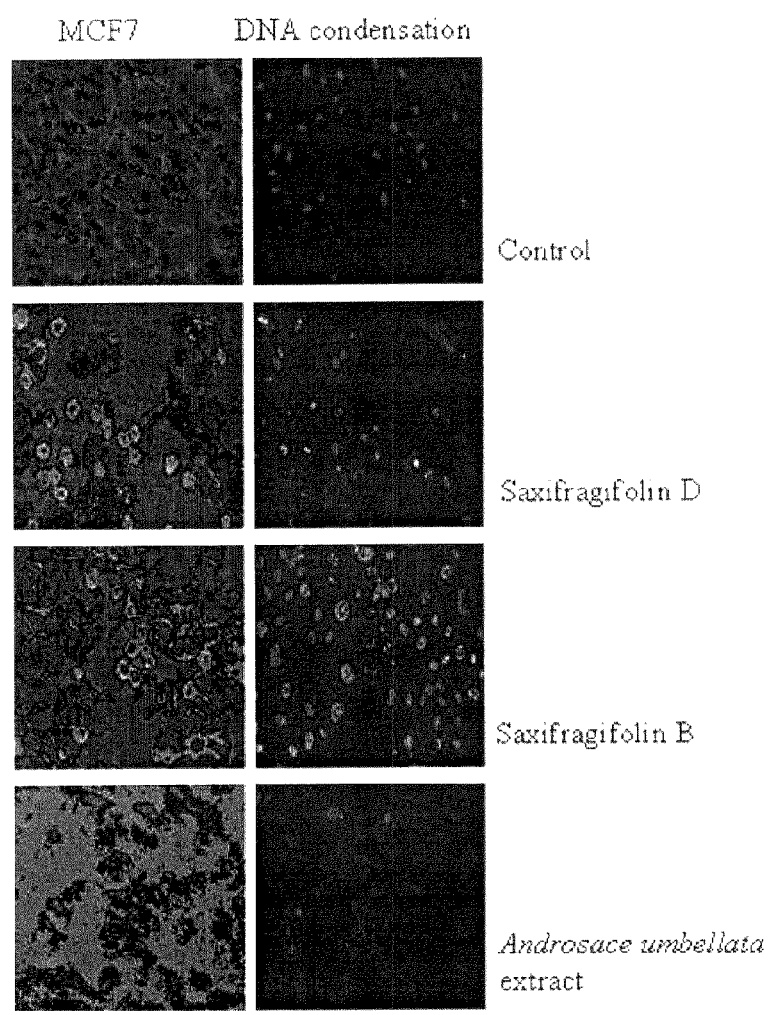
FIG. 1 shows the effect of apoptosis of MCF7 (breast cancer cells) by the *Androsace umbellata* Merr. extract and saxifragifolins saxifragifolin D of the present invention.

The cells were cultured on a 96-well plate, $10^4$ cells each. After treating with the extract and the active ingredient at a concentration of 0, 1, 10 and 100 μg/mL, the cells were cultured for 24 hours. After washing with PB (phosphate-buffered saline), the cells were treated with Hoechst stain (100 μg/mL PBS). After 10 minutes, the cells were observed under a fluorescent microscope. As seen in FIG. 1, the apoptosis-induced MCF7 breast cancer cells (apoptic bodies) were strongly stained by the Hoechst stain.

Example 3

Toxicity Test

Toxicity test was performed as follows for the *Androsace umbellata* Merr. extract, fraction thereof and saxifragifolins B and D of the present invention.

Each of the *Androsace umbellata* Merr. extract, fraction thereof and saxifragifolins D and B was dissolved in 1% sodium carboxymethlycellulose and diluted with water. The solution was intraperitoneally injected to mice (10 per each group) at a dose of 0, 0.016, 0.8, 4, 20 and 100 mg/kg. The mice were observed for 7 days. No mouse died in the *Androsace umbellata* Merr. extract group. All the 10 mice of the 100 mg/kg *Androsace umbellata* Merr. fraction group died right after the administration and two died in the 20 mg/kg group. 3 mice died in each of the 20 mg/kg saxifragifolin B and saxifragifolin D groups. No more mice died until the 7th day. The cause of the death of the mice in the *Androsace umbellata* Merr. extract, fraction, saxifragifolin B and saxifragifolin D groups was the hemolysis of red blood cells due to the high blood level right after the intraperitoneal injection. When the *Androsace umbellata* Merr. extract, fraction thereof and saxifragifolins D and B were dissolved in corn oil and orally administered at a dose of 1, 10 and 100 mg/kg, no mice died for 7 days.

Preparation Example 1

Preparation of Tablets

A tablet containing 15 mg of the *Androsace umbellata* Merr. extract, fraction thereof, saxifragifolin D, saxifragifolin B or a mixture thereof as an active ingredient was prepared as follows.

250 g of the active ingredient was mixed with 175.9 g of lactose, 180 g of potato starch and 32 g of colloidal silicon dioxide. After adding 10% gelatin solution, the mixture was ground and passed through a 14-mesh sieve. After drying, the mixture obtained by adding 160 g of potato starch, 50 g of talc and 5 g of magnesium stearate was prepared into a tablet.

Preparation Example 2

Preparation of Capsule 500 mg of the active ingredient (*Androsace umbellata* Merr. extract, fraction thereof, saxifragifolin D, saxifragifolin B or a mixture thereof) was filled in a hard gelatin capsule.

Preparation Example 3

Preparation of Injectable 200 mg of the active ingredient (*Androsace umbellata* Merr. extract, fraction thereof, saxifragifolin D, saxifragifolin B or a mixture thereof) was dissolved in 200 mg of physiological saline containing polyoxyethylene hydrogenated castor oil by heating.

INDUSTRIAL APPLICABILITY

As apparent from the above description, the present invention relates to an anticancer agent comprising an *Androsace umbellata* (Lour.) Merr. extract, fraction thereof and saxifragifolin B or saxifragifolin D isolated therefrom as an active ingredient. The *Androsace umbellata* Merr. extract, which contains saxifragifolin, a triterpene saponin compound, inhibits the growth of cancer cells and induces the apoptosis of cancer cells with few side effects and, thus, can be utilized for prevention and treatment of cancers.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A method of treating cancer, selected from the group consisting of lung cancer, colon cancer, breast cancer and uterine cancer, in a patient in need thereof which comprises administering a pharmaceutically effective amount of the anticancer agent comprising saxifragifolin D represented by the following formula (1),

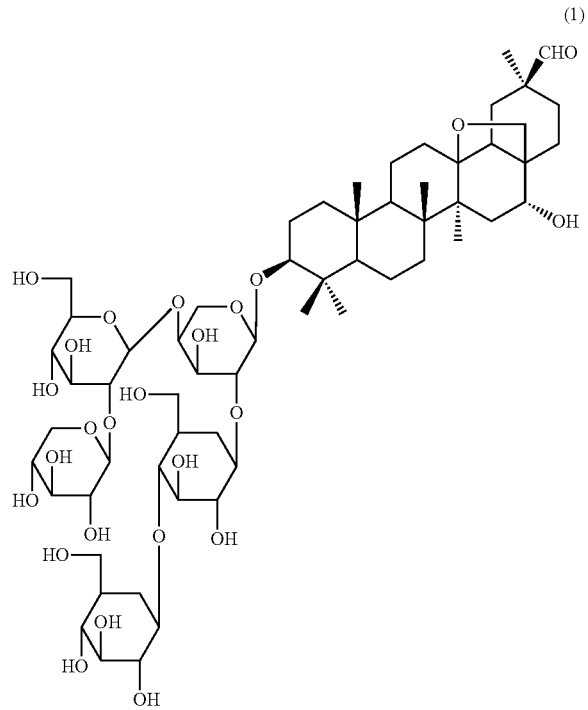

which is isolated from *Androsace umbellata* (Lour.) Merr. extract or a fraction thereof.

2. The method of treating cancer of claim 1, wherein the cancer is lung cancer.

3. The method of treating cancer of claim 1, wherein the cancer is colon cancer.

4. The method of treating cancer of claim 1, wherein the cancer is breast cancer.

5. The method of treating cancer of claim 1, wherein the cancer is uterine cancer.

* * * * *